(12) United States Patent
Mazzola et al.

(10) Patent No.: US 7,678,923 B2
(45) Date of Patent: Mar. 16, 2010

(54) METHOD FOR SYNTHESIZING 5-CHLORO-1-ARYL-4-(4,5-DICYANO-1H-IMIDAZOL-2-YL)-3-ALKYL-1H-PYRAZOLE DERIVATIVES

(75) Inventors: Alessandro Mazzola, Cureggia (CH); Giovanni Sanso, Milan (IT)

(73) Assignee: EVULTIS, Lugano (CH)

( * ) Notice: Subject to any disclaimer, the term of this patent is extended or adjusted under 35 U.S.C. 154(b) by 851 days.

(21) Appl. No.: 10/553,399

(22) PCT Filed: Apr. 9, 2004

(86) PCT No.: PCT/IB2004/001513

§ 371 (c)(1),
(2), (4) Date: Sep. 13, 2006

(87) PCT Pub. No.: WO2004/092159

PCT Pub. Date: Oct. 28, 2004

(65) Prior Publication Data

US 2007/0155811 A1    Jul. 5, 2007

(30) Foreign Application Priority Data

Apr. 17, 2003    (FR) .................. 03 04806

(51) Int. Cl.
*A61K 31/4155* (2006.01)
*C07D 231/06* (2006.01)
*C07D 233/20* (2006.01)
(52) U.S. Cl. ............................... 548/312.4; 514/397
(58) Field of Classification Search .............. 548/312.4; 514/397
See application file for complete search history.

(56) References Cited

FOREIGN PATENT DOCUMENTS

EP    0412849    10/1990
EP    0412849  A2 *    2/1991

* cited by examiner

*Primary Examiner*—Kamal A Saeed
*Assistant Examiner*—Janet L Coppins
(74) *Attorney, Agent, or Firm*—William E. Beaumont

(57) ABSTRACT

Method for synthesising 1-aryl-4-(imidazol-2-yl)-3-alkyl-1H-pyrazole derivatives from 1-aryl-3-alkyl-1H-pyrazo-line-5-one derivatives.

25 Claims, No Drawings

METHOD FOR SYNTHESIZING 5-CHLORO-1-ARYL-4-(4,5-DICYANO-1H-IMIDAZOL-2-YL)-3-ALKYL-1H-PYRAZOLE DERIVATIVES

The present invention relates to a novel method for synthesizing 1-aryl-4-(imidazol-2-yl)-3-alkyl-1H-pyrazole derivatives from 1-aryl-3-alkyl-1H-pyrazolin-5-one derivatives.

It relates more particularly to a novel method for synthesizing 5-chloro-1-aryl-4-(4,5-dicyano-1H-imidazol-2-yl)-3-alkyl-1H-pyrazol derivatives of general formula (I):

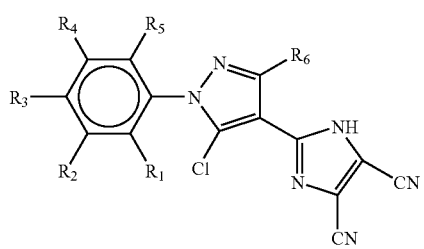

in which formula:
R₁ to R₅, which may be identical or different, represent a group chosen from:
a hydrogen atom,
a halogen atom,
a radical corresponding to the formula —(X)n-R₇ in which X represents a group chosen from oxygen, sulfur, a sulfinyl radical and a sulfonyl radical, n is equal to 0 or to 1, and R₇ represents a linear or branched, saturated or unsaturated alkyl radical optionally substituted with one or more halogen atoms, which may be identical or different, this alkyl radical comprising 1 to 4 carbon atoms.
R₆ represents a linear or branched, saturated or unsaturated alkyl radical comprising from 1 to 6 carbon atoms, optionally substituted with one or more halogen atoms, which may be identical or different.

1-arylpyrazol compounds are known to exhibit an activity against a very large number of parasites, in fields as wide and varied as agriculture, public health and veterinary medicine. Patents EP-0 234 119, EP-0 295 117 and U.S. Pat. No. 5,232, 940 disclose a class of insecticides and parasiticides derived from N-phenylpyrazols.

The compounds according to general formula (I) were disclosed in European application EP-0 412 849 for their pesticidal and insecticidal activity, in particular for combating, in the field of veterinary medicine and of livestock rearing, arthropods and helminths that are internal or external parasites of vertebrates. They are particularly useful for combating these parasites in warm-blooded vertebrates, humans and animals such as members of the ovine race, cattle, members of the horse family, pigs, dogs and cats.

According to European application EP-0 412 849, the compounds according to general formula (I) are prepared according to the scheme given in FIG. 1, from 1-aryl-3-alkyl-1H-pyrazolin-5-one derivatives, themselves obtained conventionally from arylhydrazine and the corresponding ethyl 3-alkyl-3-oxopropanoate.

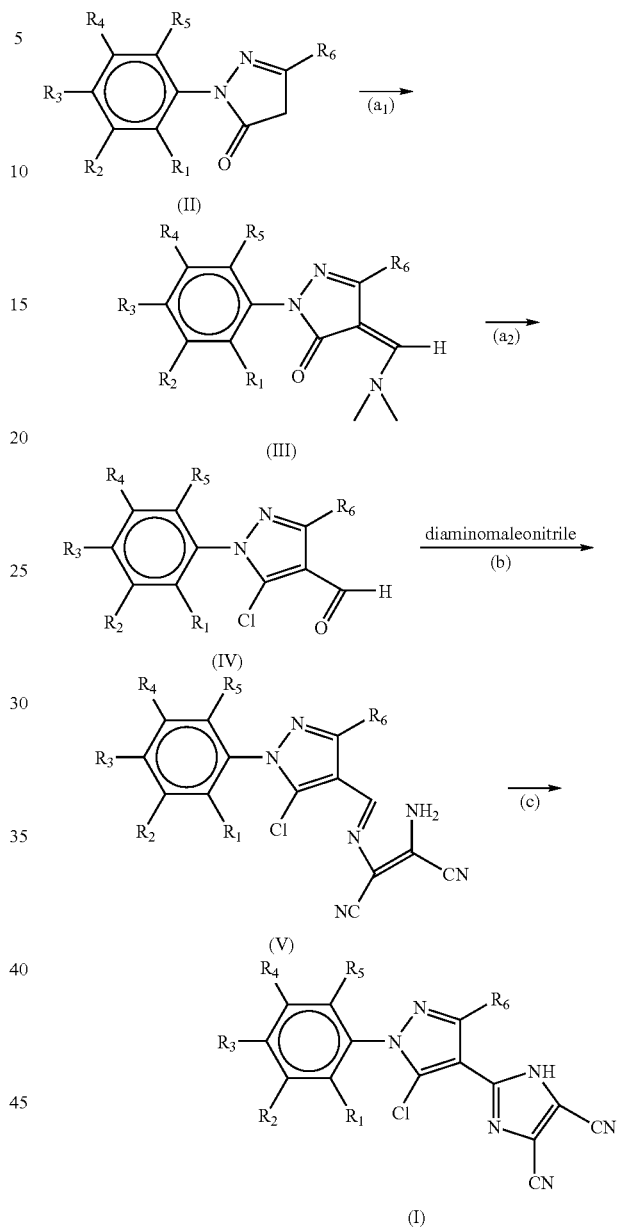

According to the method of the prior art, the pyrazoline derivative is subjected to the action of the Vilsmeier reagent so as to induce a formylation reaction and make it possible to obtain the corresponding 5-chloro-4-carboxaldehyde, corresponding to general formula (IV), via the formation, isolation and purification of the corresponding 4-[(dimethylamino) methylidene] derivative, which corresponds to general formula (III).

The conversion of the pyrazolin-5-one derivative (II) to the 5-chloro-4-carboxaldehyde derivative (IV) is carried out in two steps requiring an intermediate purification and a purification of the finished product, by chromatography on a silica gel column.

The conversion of the aldehyde (IV) to a derivative according to general formula (I) is proposed via the intermediate 4-[(2-amino-1,2-dicyanoethenylimino)-methyl] corresponding to general formula (V), obtained by condensation of the aldehyde (IV) with diaminomaleonitrile. The imine (V) gives the derivative according to general formula (I) via an oxidative cyclization, which is carried out by means of the N-chlorosuccinimide/nicotinamide couple or, failing this, using 2,3-dichloro-5,6-dicyano-1,4-benzoquinone.

A subject of the present application is a novel method for the conversion of the products corresponding to general formula (II) to products according to the general formula (I), in which formulae the variables $R_1$ to $R_6$ have the same definition as above, this method having fewer steps compared with the methods of the prior art and requiring the use of fewer purifications. In addition, the method has better yields.

The method of the invention, illustrated by FIG. 2 below, is characterized in that:
(a) in a first step, the pyrazolin-5-one derivative (II) is converted to the 1-aryl-3-alkyl-4-carboxaldehyde-5-chloropyrazol derivative of formula (IV) in one step by Vilsmeier treatment in the presence of $POCl_3$ and DMF,
(b) in a second step, the aldehyde (IV) is converted to the 1-aryl-3-alkyl-4-[(2-amino-1,2-dicyanoethenylimino) methyl]-5-chloropyrazole corresponding to general formula (V) by condensation of the aldehyde (IV) with diaminomaleonitrile,
(c) in a third step, the imine (V) gives the derivative according to general formula (I) via oxidative cyclization, which is carried out by treatment with a hypochlorite.

The invention relates more particularly to the derivatives corresponding to formula (I) in which n=0.

Advantageously, one or more of the following conditions are met:
$R_1$ to $R_5$, which may be identical or different, represent a group chosen from:
a hydrogen atom,
a halogen atom,
a linear or branched, saturated or unsaturated alkyl radical $R_7$ optionally substituted with one or more halogen atoms, which may be identical or different, this alkyl radical comprising 1 to 4 carbon atoms,
$R_6$ represents a linear or branched, saturated or unsaturated alkyl radical comprising from 1 to 4 carbon atoms.

More preferably, one or more of the following conditions are met:
$R_1$ to $R_5$, which may be identical or different, represent a group chosen from:
a hydrogen atom,
a chlorine atom,
a linear or branched, saturated or unsaturated alkyl radical $R_7$ optionally substituted with one or more fluorine atoms, this alkyl radical comprising 1 to 4 carbon atoms,
$R_6$ represents a radical chosen from methyl, ethyl, tert-butyl and isopropyl.

According to a preferred embodiment of the invention, the latter applies to the preparation of a product chosen from:
5-chloro-1-(2,6-dichloro-4-trifluoromethylphenyl)-4-(4,5-dicyano-1H-imidazol-2-yl)-3-methyl-1H-pyrazol,
5-chloro-1-(2,6-dichloro-4-trifluoromethylphenyl)-4-(4,5-dicyano-1H-imidazol-2-yl)-3-isopropyl-1H-pyrazol,
5-chloro-1-(2,6-dichloro-4-trifluoromethylphenyl)-4-(4,5-dicyano-1H-imidazol-2-yl)-3-ethyl-1H-pyrazol,
5-chloro-1-(2,6-dichloro-4-trifluoromethylphenyl)-4-(4,5-dicyano-1H-imidazol-2-yl)-3-tert-butyl-1H-pyrazol.

The prior art teaches the existence of some general methods for incorporating a 4,5-dicyano-1H-imidazol-2-yl group into an aliphatic or heterocyclic structure using diaminomaleonitrile. It is possible, according to R. W. Begland, *J. Org. Chem.* 39 (16), 2341, 1974, to use orthoesters or orthoamides, to intermediately prepare derivatives from monocondensation of diaminomaleonitrile with acid chlorides or anhydrides, or to involve the formation of a Schiff's monobase followed by an oxidative cyclization.

The method of the invention provides reaction conditions that make it possible to avoid the isolation and purification of the intermediate (III). These reaction conditions comprise a method of oxidative cyclization that is more suited and can be more readily adapted to an industrial scale for the final step.

According to a preferred variant of the method of the invention, it is possible to convert the pyrazolones corresponding to general formula (II) to the derivatives according to general formula (I) by isolating and purifying only the aldehyde intermediate (IV), i.e. in only two steps, under conditions that are particularly in accordance with industrial use and with extremely competitive yields.

The improvements and modifications that are the subject of the present invention, shown diagrammatically in FIG. 2, are given in detail as follows:

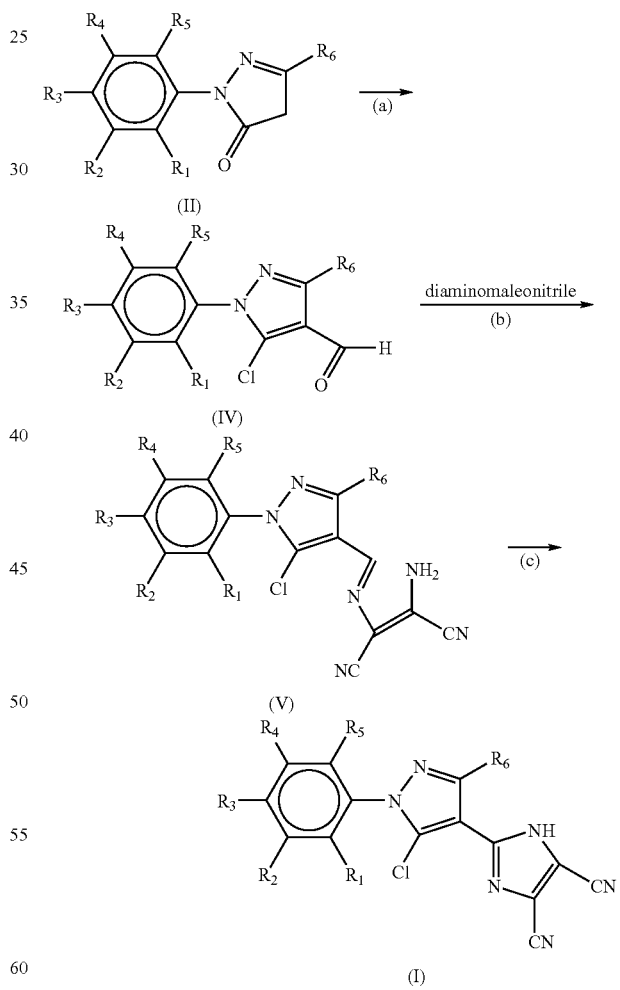

FIG. 2

Steps ($a_1$) and ($a_2$) according to FIG. 1 are advantageously replaced with a single step (a) as illustrated in FIG. 2.

The Vilsmeier reagents, normally used for the introduction of a carboxaldehyde function onto a heterocyclic unit, are generally prepared via the reaction of an N,N-dialkylamide, such as N,N-dimethylformamide, with a condensation and (or) dehydration reagent. The preferred reagents are, for example, oxalyl chloride, phosgene or phosphoryl trichloride, used in solvents of the nonprotic type, and in particular chlorinated solvents.

According to the method of the invention, step (a) is carried out by treatment of the compound of formula (II) in DMF in the presence of 20 to 40 molar equivalents of $POCl_3$, preferably 25 to 35 molar equivalents of $POCl_3$, even more preferably 30 molar equivalents of $POCl_3$.

This reaction is advantageously carried out in the presence of a (II)/DMF ratio ranging from 1 to 2, even more advantageously from 1 to 1.5, and preferably from 1 to 1.2.

These reaction conditions make it possible:
to obtain the product (IV) without intermediate isolation and purification of the product of formula (III);
to limit the volume of waste and therefore to reduce the environmental constraints;
to obtain the product (IV) with a yield of 85% after purification by chromatography on a silica column, while the method of the prior art gave only a 50% yield on these steps and required the use of approximately 250 molar equivalents of $POCl_3$ (EP-0 412 489).

Step (b) according to FIG. 2 is improved compared with step (b) according to FIG. 1, as mentioned in European application EP-0 412 849. The formation of the imine according to general formula (V) is usually carried out in a solvent medium such as aromatic solvents, and more specifically benzene or toluene, in a chlorinated solvent medium or aliphatic alcohols, such as methanol or ethanol, at a temperature of between 0 and 70° C.

According to the method of the invention, the reaction is preferably carried out in a methanolic medium with acid catalysis. Among the acids that can be used, mention may be made of: acetic acid, para-toluenesulfonic acid, trifluoroacetic acid, sulfuric acid and methanesulfonic acid.

According to a preferred embodiment of the present invention, the reaction is catalyzed by trifluoroacetic acid, and makes it possible to obtain a virtually quantitative yield in step (b).

Step (c) as illustrated in FIG. 2 is carried out by treatment of the compound corresponding to formula (V) with a hypochlorite, such as an alkali metal or alkaline-earth metal hypochlorite or an alkyl hypochlorite. Among the hypochlorites that can be used in the method of the invention, mention may, for example, be made of: tert-butyl hypochlorite, sodium, hypochlorite, calcium hypochlorite and lithium hypochlorite. The reaction is generally carried out in a hydroxylated aliphatic solvent, at a temperature of between −5° C. and 25° C., preferably of between 0° C. and 5° C.

Advantageously, 1 to 5 molar equivalents of hypochlorite relative to the product (V), even more preferably 2 to 3 molar equivalents, are used. Among the solvents that can be used for carrying out this step, mention may be made of: methanol, ethanol and propanol.

According to the methods of the prior art, the oxidative cyclization of the imine of formula (V) was carried out (EP-0 412 849) by treatment with the N-chlorosuccinimide, nicotinamide couple, nicotinamide being a potentiator of the oxidizing activity of NCS (cf. O. Moriya et al., Synthesis, (1984), 12, p. 1057-58).

Through the same authors, it is known that 2,3-dichloro-5,6-dicyano-1,4-benzoquinone and diimino-succinonitrile have low reactivity, these oxidizing reagents requiring reaction times at reflux in acetonitrile that can range from 17 hours to 4 days for the oxidative cyclization of these same Schiff's bases. Under the conditions recommended by O. Moriya, the conversion of a product (V) to a product according to general formula (I) is carried out with a yield limited to 56% after chromatography on silica gel. The use of such a couple in fact requires a difficult purification, the resulting crude product containing three nitrogenous heterocycles with similar polarities.

According to the same European application EP-0 412 849, the cyclization can also be carried out with DDQ or 2,3-dichloro-5,6-dicyano-1,4-benzoquinone, a reagent whose industrial use is limited. Furthermore, the by-product formed, i.e. the corresponding 1,4-dihydroxybenzene, is not devoid of toxicity and requires significant treatment of the aqueous waste. It is known, moreover, that this reagent does not in general offer an appreciable conversion rate, that it induces marked coloration of the resulting product, and that it requires a long reaction time and the selection of a high reaction temperature, for example at the reflux of acetonitrile. These observations and characteristics are in particular found in U.S. Pat. No. 5,380,865, for a similar reaction using this oxidizing agent and 1-amino-2-(2,6-dichloro-4-trifluoromethylbenzylideneamino)-1,2-dicyanoethylene, and producing the corresponding 2-aryl-4,5-dicyanoimidazol in the form of a brown solid with a yield of 42.5%.

The prior art mentions many reagents other than those mentioned above which have been proposed for the oxidative cyclization of the corresponding Schiff's base (product (V)). U.S. Pat. No. 5,380,865 proposes in general, for obtaining 2-aryl-4,5-dicyanoimidazol derivatives, the use of the combinations iodine-sodium acetate or bromine-sodium acetate in an inert solvent such as dichloromethane or dimethylformamide. The use of lead tetraacetate is recommended for the same conversion by T. Eicher et al., Tetrahedron Lett., (1980), 21, 3751-54 and in U.S. Pat. No. 4,220,466 for obtaining, respectively, 2-isopropyl-4,5-dicyano-imidazol and 2-tert-butyl-4,5,dicyanoimidazol.

The use of diiminosuccinonitrile is mentioned for the preparation of 2-tert-butyl-4,5-dicyanoimidazol, in an acetonitrile medium at reflux, with a yield of 57%, by R. W. Begland et al., Chem. (1974), 39, p. 2341-2350.

It has been reported, by J. P. Ferris, J. Org. Chem., 52(12), 2355-61, (1987), that tert-butyl hypochlorite can, in an ethyl acetate medium and under relatively mild conditions, contribute to the conversion of an acyclic ribose derivative incorporating an iminoamino-maleonitrile residue to a 2-substituted-4,5-dicyanoimidazol derivative, with a yield of 66%. The use of N-bromosuccinimide in an ethyl acetate medium and at a moderate temperature was clearly mentioned for a similar conversion and the same yield in the same document.

However, contrary to the teaching of the latter document, the use of hypochlorite for carrying out step (c) of the method of the invention gives results that are far superior in terms of yield compared with the use of N-halosuccinimide (comparative example 5-2). In the method of the invention, a rate of conversion of the compounds of formula (V) to the compounds of formula (I) is obtained that is far greater than could be hoped for from the abovementioned publication.

The use of a hypochlorite for this step has many advantages. Hypochlorites are products that are more widely used in industry compared with most of the reagents mentioned in the prior art. The costs of these hypochlorites is also much more attractive than that of the reagents of the prior art.

The reagent that is particularly preferred according to the present invention for step (c)/FIG. 2 is sodium hypochlorite. The use of a sodium hypochlorite having an active chlorine content in the region of 150 g/liter (such as that sold by Solvay Electrolyse) or the use of a guaranteed product with an active chlorine content of 315 g/liter (such as that sold by Atofina, Chlorochimie [Chlorochemistry] division) is more specifically chosen. Unlike the reagents previously mentioned in the prior art for this conversion, hypochlorites react under milder temperature conditions and with faster kinetics. As a matter of interest, mention may be made of the two examples mentioned above and using 2,3-dichloro-5,6-dicyanobenzoquinone in acetonitrile for the oxidative cyclization, in application EP-0 412 849 as in the publication *Synthesis*, (1984), 12, p. 1057-58, with conversion of the imine at reflux and, respectively, in a minimum of 12 and 17 hours.

The use of the sodium hypochlorite corresponding to the characteristics mentioned above makes it possible to limit the conversion time to 0.5 hr and, through a judicious choice of the volume of solvent, in particular of methanol, to virtually exclusively promote the elimination of hydrochloric acid from the intermediate chloramine at the expense of regeneration of the aldehyde of origin.

According to this variant of the invention, the product of general formula (V) is treated:

in methanol, at a molar concentration of (V) ranging from 0.005 M to 0.1 M, advantageously from 0.01 M to 0.08 M, even more preferably from 0.02 M to 0.06 M, with a hypochlorite in quality ranging from 1 to 5 molar equivalents, preferably from 2 to 3 molar equivalents, with respect to the product (V), this hypochlorite being in an aqueous solution having a concentration ranging from 1 to 5 M, preferably from 2 to 5 M.

Furthermore, unlike the reagents according to the prior art, the hypochlorites, under the conditions of use employed in the method according to the present invention, do not engender the formation of aromatic and/or heterocyclic by-products, the elimination of which is laborious and expensive.

According to a particularly attractive variant of the method according to the present invention, the 1-aryl-3-alkyl-1H-pyrazolin-5-ones according to general formula (II) are converted to a product corresponding to general formula (I) according to a reaction series limited to two steps, the only intermediate isolated and purified being the aldehyde corresponding to general formula (IV).

The reaction scheme is represented in FIG. 3:

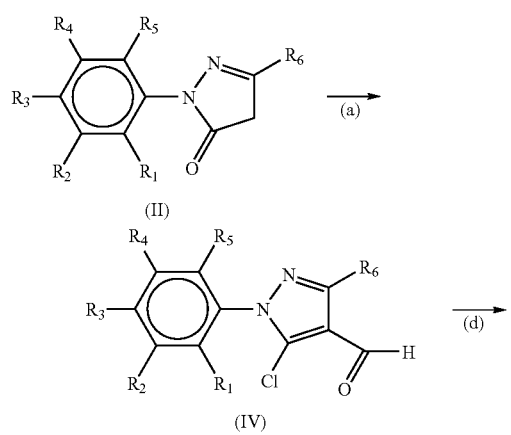

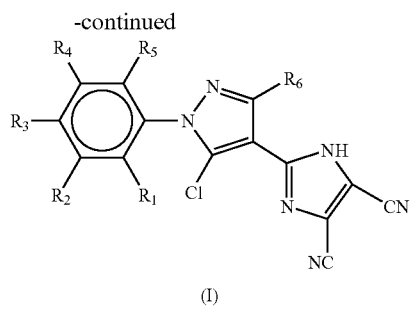

According to this scheme, step (a) is identical to that shown in FIG. 2 and given in detail above. Step (d) according to the same scheme illustrated in FIG. 3 does not comprise any step for purifying the intermediate imine corresponding to general formula (V) and therefore comes instead and in place of steps (b) and (c) according to FIG. 2. This reduction in the number of steps is permitted by the definition and the choice of a single-phase reaction system able to promote in continuity the formation of the imine and the oxidative cyclization, the oxidizing agent preferably chosen being sodium hypochlorite.

According to this scheme:

(a) in a first step, the pyrazolin-5-one derivative (II) is converted to the 1-aryl-3-alkyl-4-carboxaldehyde-5-chloropyrazol derivative of formula (IV) in one step by Vilsmeier treatment in the presence of POCl$_3$ and DMF, (d) in a second step, by successive treatment of the compound of formula (IV) with diaminomaleonitrile and then with a hypochlorite.

This variant makes it possible to obtain yields ranging up to more than 85% over step (d).

One of the particularly preferred variants of the method according to the present invention therefore consists in directly converting the 1-aryl-3-alkyl-1H-pyrazolin-5-ones according to general formula (II) according to the operation shown schematically by step (a)/FIG. 2 or 3, as explained above, and then in purifying the crude product obtained by flash chromatography on silica gel, and in converting the corresponding aldehyde according to general formula (IV) to a product according to general formula (I), according to step (d)/FIG. 3. This conversion is carried out in a hydroxylated aliphatic solvent medium, preferably a methanol, with, firstly, for the formation of the imine with diaminomaleonitrile, a molar concentration of substrate of between 0.15 and 0.2 M, preferably 0.18 M, with acid catalysis, preferably provided by trifluoroacetic acid, present in proportions of between 0.02 and 0.2 molar equivalent, preferably 0.1 molar equivalent, and then, secondly, for the oxidative cyclization and the formation of the imidazolyl ring, dilution to a molar concentration of substrate of between 0.01 and 0.08 M, preferably 0.04 M, and the use of 2 to 3 molar equivalents of sodium hypochlorite having a concentration ranging from 2 M to 5 M, preferably 2 molar equivalents of the 2.3 M industrial product.

The examples illustrate the characteristics and the advantages of the method according to the present invention without limiting the scope thereof.

EXAMPLE 1

Preparation of 1-(2,6-dichloro-4-trifluoro-methylphenyl)-3-methyl-1H-pyrazolin-5-one (IIa)

5.27 g of ethyl acetoacetate (40.5 mmol) are run into, at ambient temperature, a solution of 9.8 g of 2,6-di-chloro-4-trifluoromethylphenylhydrazine (40 mmol) in 50 ml of glacial acetic acid, and the mixture is brought to reflux for 3 hours without stirring. Stirring is maintained during the return to ambient temperature before elimination of the solvent under reduced pressure. The residue is solidified from 80 ml of hexane in order to thus obtain the title product with a yield of 85%, which product has the following characteristics:

melting point: 169-170° C., $^1$H NMR (CDCl$_3$): 2.02 (s, 3H) H$_6$; 3.25 (s, 2H) H$_4$; 7.5 (s, 2H) H$_9$ H$_{9'}$. $^{13}$C NMR: 18.0 (C$_6$); 41.5 (C$_4$); 123.0 (q, J$_{C-F}$=273.4 Hz, C$_{11}$); 126.6 (q, J$_{C-F}$=3.6 Hz, C$_9$, C$_{9'}$); 133.8 (q, J$_{C-F}$=34.4 Hz, C$_{10}$); 136.6 (C$_7$); 137.1 (C$_8$, C$_{8'}$); 158.6 (C$_3$); 171.9 (C$_5$). $^{19}$F NMR: −63.7.

For a better understanding of the data compiled above and in the following examples, an atomic numbering was selected that can be found in the structure presented in example 4.

EXAMPLE 2

Preparation of 5-chloro-1-(2,6-dichloro-4-trifluoromethylphenyl)-3-methyl-1H-pyrazole-4-carboxaldehyde (IVa), according to eq. A/FIG. 2

100 ml of POCl$_3$ (1.09 mol) are introduced into a 500 ml round-bottomed flask equipped with a condenser and a dropping funnel. The temperature is brought to between 0 and 5° C. so as to slowly run in 2.8 ml of N,N-di-methylformamide (36.3 mmol). After a return to ambient temperature in 10 to 15 minutes, 11.3 g (36.3 mmol) of pyrazolone (IIa) are added. After dissolution, the entire mixture is refluxed for 16 hours. The reaction mixture is then poured slowly into 1.5 liters of ice-cold water and neutralized with sodium carbonate.

The resulting precipitate is recovered by filtration. Purification by flash chromatography on silica gel is then performed, elution being carried out with an ethyl acetate/pentane (5/95) mixture, so as to obtain 11.2 g of the title product with a yield of 86%, which product has the following characteristics:

melting point: 76° C.

$^1$H NMR (CDCl$_3$): 2.55 (s, 3H) H$_6$; 7.80 (s, 2H) H$_9$, H$_{9'}$; 10.0 (s, 1H) H$_{12}$. $^{13}$C NMR: 14.8 (C$_6$); 117.7 (C$_5$); 122.8 (q, J$_{C-F}$=274.2 Hz, C$_{11}$); 126.7 (q, J$_{C-F}$=4.0 Hz, C$_9$, C$_{9'}$); 135.2 (q, J$_{C-F}$=34.4 Hz, C$_{10}$); 136.4 (C$_4$); 136.7 (C$_7$); 137.2 (C$_8$, C$_{8'}$); 154.1 (C$_3$); 184.0 (C$_{12}$). $^{19}$F NMR: −63.7.

Comparitive Example 2

Preparation of 5-chloro-1-(2,6-dichloro-4-trifluoromethylphenyl)-3-methyl-1H-pyrazole-4-carboxaldehyde (IVa), according to eqs. a$_1$ and a$_2$/FIG. 1

127 ml of POCl$_3$ (1.39 mol) are introduced into a 500 ml round-bottomed flask equipped with a condenser and a dropping funnel. The temperature is brought to between 0 and 5° C. so as to slowly run in 3.09 g (42.2 mmol) of N,N-dimethylformamide. After a return to ambient temperature in 10 to 15 minutes, 11.3 g (36.3 mmol) of pyrazolone (IIa) are added. The entire mixture is refluxed for 30 minutes, the excess POCl$_3$ is eliminated under reduced pressure, and the residue is carefully run into ice-cold water. After neutralization with sodium carbonate and extraction with ether, the residue is purified by flash chromatography on silica gel, elution being carried out with a methanol/methylene chloride (2/98) mixture. 7.85 g of the intermediate (IIIa), i.e. 1-(2,6-dichloro-4-trifluoromethylphenyl)-3-methyl-4-((dimethylamino)methylidene)-1H-pyrazolin-5-one, are thus obtained.

The 7.85 g of this intermediate (21.4 mmol) are taken up for treatment at reflux for 2 hours in 240 ml of POCl$_3$ (4.59 mol), followed by stirring at ambient temperature maintained for 18 hours. The excess POCl$_3$ is eliminated under reduced pressure, and the residue is carefully run into ice-cold water. After neutralization with sodium carbonate and extraction with ether, the residue is purified by flash chromatography on silica gel, elution being carried out with an ethyl acetate/pentane (5/95) mixture, so as to give 6.6 g of the title product, i.e. with an overall yield in the region of 51%.

Characteristics of the intermediate (IIIa):

melting point: 201° C., $^1$H NMR (CDCl$_3$): 2.20 (s, 3H) H$_6$; 3.31 (s, 3H) and 3.85 (s, 3H) for the two methyl radicals (N—CH$_3$); 7.18 (s, 1H) H$_{12}$; 7.65 (s, 2H) H$_9$, H$_{9'}$. $^{13}$C NMR: 4.5 (C$_6$); 44.2 and 48.8 for the two methyl radicals (N—CH$_3$); 98.1 (C$_4$); 123.6 (q, J$_{C-F}$=273.4 Hz, C$_{11}$); 126.4 (q, J$_{C-F}$=3.6 Hz, C$_9$, C$_{9'}$); 133.8 (q, J$_{C-F}$=34.4 Hz, C$_{10}$); 137.6 (C$_7$); 138.7 (C$_8$, C$_{8'}$); 152.7 (C$_3$); 153.4 (C$_{12}$), 163.1 (C$_5$). $^{19}$F NMR: −63.7.

EXAMPLE 3

Preparation of 4-((2-amino-1,2-dicyanoethenylimino)methyl)-5-chloro-1-(2,6-dichloro-4-trifluoro-methylphenyl)-3-methyl-1H-pyrazole (Va), according to eq. b/FIG. 2

A solution of 16.1 g of aldehyde (IVa) (45 mmol) and of 5 g of diaminomaleonitrile (46.3 mmol) in 200 ml of methanol is prepared in a 500 ml round-bottomed flask equipped with a condenser. 0.35 ml of trifluoroacetic acid, i.e. 10 mol %, is added to this solution with stirring. The stirring is prolonged at ambient temperature for 30 minutes and then at reflux for 1 hour, before cooling and elimination of the solvents under reduced pressure.

The crude product is solidified and dried. 19.7 g of the title product are thus obtained, with a yield in the region of 98%. This product corresponds to the physical characteristics mentioned below:

melting point: 199° C., $^1$H NMR (CDCl$_3$): 2.55 (s, 3H) H$_6$; 5.30 (s, 2H) H$_{15}$; 7.80 (s, 2H) H$_9$, H$_{9'}$; 8.40 (s, 1H) H$_{12}$. $^{13}$C NMR: 15.8 (C$_6$); 109.2, 112.8, 114.3 (C$_{14}$, C$_{15}$ or C$_{15'}$); 115.5 (C$_5$); 122.8 (q, J$_{C-F}$=273.6 Hz, C$_{11}$); 125.1 (C$_{14'}$); 126.7 (q, J$_{C-F}$=4.0 Hz, C$_9$, C$_{9'}$); 133.9 (C$_4$); 135.1 (q, J$_{C-F}$=34.4 Hz, C$_{10}$); 136.7 (C$_7$); 137.2 (C$_8$, C$_{8'}$); 150.2 (C$_{12}$); 152.3 (C$_3$). $^{19}$F NMR: −63.7.

EXAMPLE 4

Preparation of 5-chloro-1-(2,6-dichloro-4-trifluoromethylphenyl)-4-(4,5-dicyano-1H-imidazol-2-yl)-3-methyl-1H-pyrazole (Ia), according to eq. c/FIG. 2, with tBuOCl

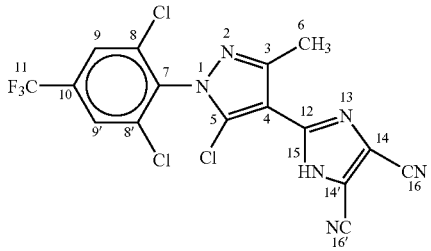

8 g of imine (Va) (17.9 mmol) are introduced into a 500 ml round-bottomed flask equipped with a dropping funnel and brought to a temperature of between 0 and 5° C. A solution of 2.33 g of tert-butyl hypochlorite (21.5 mmol) in 180 ml of ethyl acetate is run in with stirring. The resulting solution is stirred at 0° C. for 90 minutes and then at ambient temperature for 2 hours. The reaction mixture is diluted with 80 ml of water and then extracted with dichloromethane. The resulting organic phase is washed three times with water and then dried over magnesium sulfate. After elimination of the solvent under reduced pressure, the residue is purified by flash chromatography on silica gel, eluting with a methanol/methylene chloride (2/98) mixture, to give 6.7 g of the title product, with a yield of 83%. This product corresponds to the physical characteristics mentioned below:

melting point: 98° C.

$^1$H NMR (CDCl$_3$): 2.68 (s, 3H) H$_6$; 7.80 (s, 2H) H$_9$; 10.80 (s, 1H) H$_{15}$. $^{13}$C NMR: 15.6 (C$_6$); 108.0 (C$_{16}$, C$_{16'}$); 111.0 (C$_{14}$, C$_{14'}$); 122.6 (q, J$_{C-F}$=271.7 Hz, C$_{11}$); 126.8 (q, J$_{C-F}$=3.8 Hz, C$_9$, C$_{9'}$); 129.3 (C$_4$); 135.3 (q, J$_{C-F}$=34.6 Hz, C$_{10}$); 136.6 (C$_7$); 137.2 (C$_8$, C$_{8'}$); 144.5 (C$_{12}$); 153.0 (C$_3$). $^{19}$F NMR: −63.7.

EXAMPLE 5

Preparation of 5-chloro-1-(2,6-dichloro-4-trifluoromethylphenyl)-4-(4,5-dicyano-1H-imidazol-2-yl)-3-methyl-1H-pyrazole (Ia), according to eq. c/FIG. 2, with NaOCl A solution of 8 g of imine (Va) (17.9 mmol) in 400 ml of methanol is prepared in a 500 ml round-bottomed flask equipped with a dropping funnel, and is brought to 0° C. 15.7 ml (35.8 mmol) of a 2.3 M sodium hypochlorite solution are added at the same temperature. The reaction mixture is stirred at ambient temperature for 30 minutes and then run into 1.3 liters of water. After repeated extractions with ethyl acetate, the organic phase is washed three times with water and then dried over magnesium sulfate. After elimination of the solvent under reduced pressure, the residue is purified by flash chromatography on silica gel, elution being carried out with a methanol/methylene chloride (2/98) mixture, to give 7 g of the title product, with a yield of 88%.

Comparitive Example 5

Preparation of 5-chloro-1-(2,6-dichloro-4-trifluoromethylphenyl)-4-(4,5-dicyano-1H-imidazol-2-yl)-3-methyl-1H-pyrazole (Ia), according to eq. c/FIG. 1, with DDQ A solution of 8 g of imine (Va) (17.9 mmol) and of 5.9 g (26 mmol) of 2,3-dichloro-5,6-dicyano-1,4-benzo-quinone in 140 ml of acetonitrile is brought to reflux for 18 hours in a 500 ml round-bottomed flask equipped with a condenser. The solvent is eliminated under reduced pressure, and the corresponding dark red residue is purified by flash chromatography on silica gel, elution being carried out with a methanol/methylene chloride (2/98) mixture, to give 4.3 g of the title product, with a yield of 54%.

Comparitive Example 5-2

Preparation of 5-chloro-1-(2,6-dichloro-4-trifluoromethylphenyl)-4-(4,5-di-cyano-1H-imidazol-2-yl)-3-methyl-1H-pyrazole (Ia), according to eq. c/FIG. 1, with NCS/nicotinamide 8 g of imine (Va) (17.9 mmol), 2.39 g (17.9 mmol) of N-chlorosuccinimide and 2.44 g (20 mmol) of nicotin-amide are mixed in 45 ml of N,N-dimethylformamide, in a 250 ml round-bottomed flask. The resulting solution is stirred at 55-70° C. for 1 hour, and then, after a return to ambient temperature, this solution is run into 150 ml of water. After extraction with dichloromethane, drying, and elimination of the solvent under reduced pressure, the corresponding residue is purified by flash chromatography on silica gel, elution being carried out with a methanol/methylene chloride (2/98) mixture, to give 4.5 g of the title product, with a yield of 56%.

EXAMPLE 6

Preparation of 5-chloro-1-(2,6-dichloro-4-trifluoromethylphenyl)-4-(4,5-dicyano-1H-imidazol-2-yl)-3-methyl-1H-pyrazole (Ia), according to eq. d/FIG. 3, with NaOCl A solution containing 8 g (22.4 mmol) of aldehyde (IVa) prepared according to example 2 and 2.42 g (22.4 mmol) of diaminomaleonitrile in 120 ml of methanol is prepared in a 1 liter round-bottomed flask equipped with a condenser, and 0.18 ml of trifluoroacetic acid, i.e. 10 molar equivalent %, is added. The resulting solution is stirred at ambient temperature for 30 minutes and brought to reflux for 1 hour. After a return to ambient temperature, dilution with 360 ml of methanol and cooling to a temperature in the region of 0° C., 19.6 ml (44.8 mmol) of a 2.3 M sodium hypochlorite solution are run in. The resulting solution is stirred for 30 minutes at ambient temperature, before dilution with 1.6 liters of water, and then repeated extractions with ethyl acetate are carried out. The organic phase is then washed three times with water and then dried over magnesium sulfate. After elimination of the solvent under reduced pressure, the residue is purified by flash chromatography on silica gel, elution being carried out with a methanol/methylene chloride (2/98) mixture, to give 8.2 g of the title product, with a yield of 82%. The title product is thus obtained from the pyrazole (IIa), i.e. 1-(2,6-dichloro-4-trifluoromethylphenyl)-3-methyl-1H-pyrazolin-5-one, with an overall yield of 70.5%.

EXAMPLE 7

Preparation of 5-chloro-1-(2,6-dichloro-4-trifluoromethylphenyl)-4-(4,5-dicyano-1H-imidazol-2-yl)-3-isopropyl-1H-pyrazole (Ib), according to eqs. a and d/FIG. 3

Under the conditions given in detail in example 2, using the pyrazolone (IIb), i.e. 1-(2,6-dichloro-4-tri-fluoromethylphenyl)-3-isopropyl-1H-pyrazolin-5-one, the corresponding aldehyde (IVb), i.e. more precisely 5-chloro-1-(2,6-dichloro-4-trifluoromethylphenyl)-3-iso-propyl-1H-pyrazole-4-carboxaldehyde, is obtained. The product (IVb) is converted under the conditions explained according to example 6, so as to produce the title product with an overall yield in the region of 68%, which product has a melting point of 96-99° C.

EXAMPLE 8

Preparation of 5-chloro-1-(2,6-dichloro-4-trifluoromethylphenyl)-4-(4,5-dicyano-1H-imidazol-2-yl)-3-ethyl-1H-pyrazole (Ic), according to eqs. a and d/FIG. 3

Under the conditions given in detail in example 2, using the pyrazolone (IIc), i.e. 1-(2,6-dichloro-4-tri-fluoromethylphenyl)-3-ethyl-1H-pyrazolin-5-one, the corresponding aldehyde (IVc), i.e. more precisely 5-chloro-1-(2,6-dichloro-4-trifluoromethylphenyl)-3-ethyl-1H-pyrazole-4-carboxaldehyde, is obtained. The product (IVc) is converted under the conditions explained according to example 6, so as to produce the title product with an overall yield in the region of 70%, which product has a melting point of 75-78° C.

EXAMPLE 9

Preparation of 5-chloro-1-(2,6-dichloro-4-trifluoromethylphenyl)-4-(4,5-dicyano-1H-imidazol-2-yl)-3-tert-butyl-1H-pyrazole (Id), according to eqs. a and d/FIG. 3

Under the conditions given in detail in example 2, using the pyrazolone (IId), i.e. 1-(2,6-dichloro-4-tri-fluoromethylphenyl)-4-(4,5-dicyano-1H-imidazol-2-yl)-3-tert-butyl-1H-pyrazolin-5-one, the corresponding aldehyde (IVd), i.e. more precisely 5-chloro-1-(2,6-di-chloro-4-trifluoromethylphenyl)-3-tert-butyl-1H-pyra-zole-4-carboxaldehyde, is obtained. The product (IVd) is converted under the conditions explained according to example 6, so as to produce the title product with an overall yield in. the region of 68%, which product has a melting point of 118-120° C.

The invention claimed is:

1. A method for synthesizing 5-chloro-1-aryl-4-(4,5-dicyano-1H-imidazol-2-yl)-3-alkyl-1H-pyrazol compounds of the formula (I):

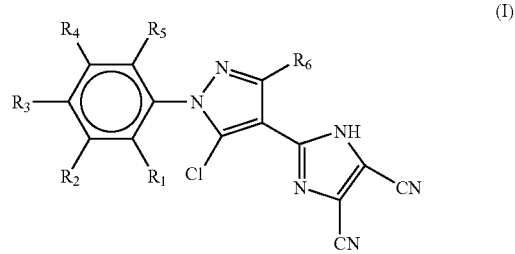

wherein:
$R_1$ to $R_5$, which are identical or different, each represent a group selected from the group consisting of:
a hydrogen atom,
a halogen atom, and
a radical corresponding to the formula $-(X)n-R_7$, in which X represents a group selected from the group consisting of oxygen, sulfur, sulfinyl radical and sulfonyl radical; n is 0 or 1; and $R_7$ represents a linear or branched, saturated or unsaturated alkyl radical optionally substituted with one or more halogen atoms, which are identical or different, the alkyl radical comprising 1 to 4 carbon atoms;
$R_6$ represents a linear or branched, saturated or unsaturated alkyl radical comprising from 1 to 6 carbon atoms, optionally substituted with one or more halogen atoms, which are identical or different, which method comprises the steps of:
(a) converting a pyrazolin-5-one compound of the formula (II) to a 1-aryl-3-alkyl-4-carboxaldehyde-5-chloropyrazol compound of the formula (IV) in one step by a Vilsmeier treatment in the presence of $POCl_3$ and DMF,
(b) converting the aldehyde of the formula (IV) to a 1-aryl-3-alkyl-4-[(2-amino-1,2-dicyanoethenylimino)methyl]-5-chloropyrazole compound of the formula (V) by condensing the aldehyde of the formula (IV) with diaminomaleonitrile, and
(c) oxidatively cyclizing the imine of the formula (V) with a hypochlorite to produce the compound of the formula I as shown below:

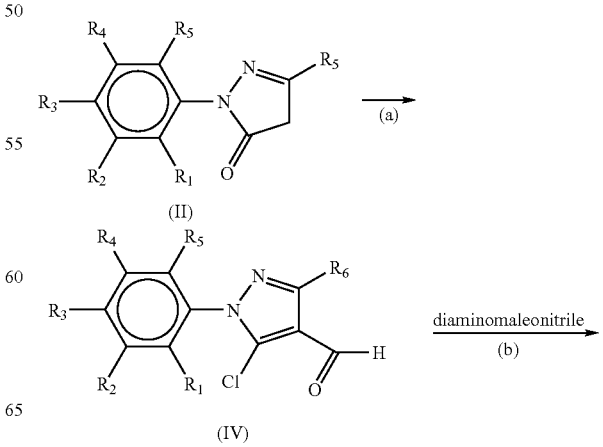

-continued

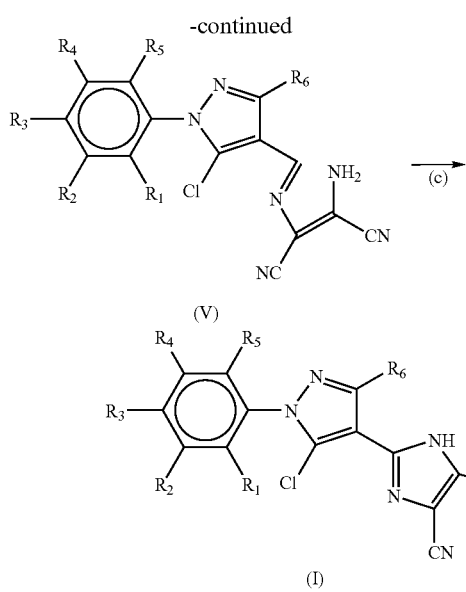

2. The method of claim 1, wherein step (a) is carried out by treating the compound of the formula (II) in DMF in the presence of 20 to 40 molar equivalents of $POCl_3$.

3. The method of claim 2, wherein step (a) is carried out by treating the compound of the formula (II) in DMF in the presence of 25 to 35 molar equivalents of $POCl_3$.

4. The method of claim 3, wherein step (a) is carried out by treating the compound of the formula (II) in DMF in the presence of 30 molar equivalents of $POCl_3$.

5. The method of claim 2, wherein the (II)/DMF ratio is between 1 and 2.

6. The method of claim 5, wherein the ratio of (II/DMF) is between 1-1.2.

7. The method of claim 1, wherein step (b) is carried out in a solvent medium at a temperature of between 0 and 70° C.

8. The method of claim 1, wherein step (b) is carried out in a methanolic medium with acid catalysis.

9. The method of claim 8, wherein the catalyst is trifluoroacetic acid.

10. The method of claim 1, wherein step (c) is carried out by treating the compound of the formula (V) with a hypochlorite comprising an alkali metal or alkaline-earth metal hypochlorite or an alkyl hypochlorite, in a hydroxylated aliphatic solvent, at a temperature of between –50° C. and 25° C.

11. The method of claim 10, wherein the temperature is between 0° C. and 5° C.

12. The method of claim 10, wherein the hypochlorite is sodium hypochlorite.

13. The method of claim 1, wherein step (c) is carried out by treating the compound of the formula (V) with 1 to 5 molar equivalents of hypochlorite relative to the compound of the formula (V).

14. The method of claim 13, wherein step (c) is carried out by treating the compound of the formula (V) with 2 to 3 molar equivalents of hypochlorite relative to the compound of the formula (V).

15. The method of claim 1, wherein the compound of the formula (V) is treated:
in methanol,
at a molar concentration of (V) ranging from 0.005 M to 0.1 M,
with a hypochlorite in an amount ranging from 1 to 5 molar equivalents with respect to the compound of the formula (V), the hypochlorite being in an aqueous solution having a concentration ranging from 1 to 5 M.

16. The method of claim 15, wherein the compound of the formula (V) is treated in methanol at a molar concentration ranging from 0.01M to 0.08M.

17. The method of claim 16, wherein the compound of the formula (V) is treated in methanol at a molar concentration ranging from 0.02 M to 0.06M.

18. The method as claimed in claim 1, wherein steps (b) and (c) are carried out in a single step (d), in the same reactor, without isolation of the intermediate product (V), as shown in the reaction scheme below:

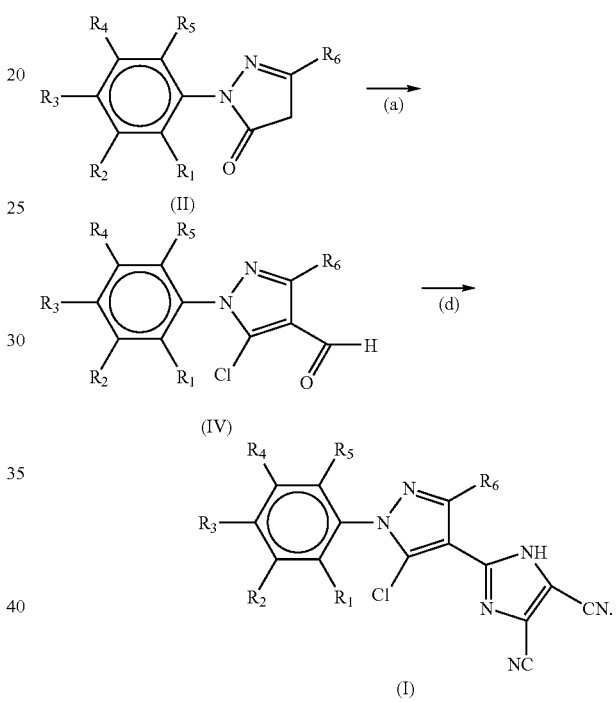

19. The method of claim 18, which comprises:
(a) in a first step, converting the pyrazolin-5-one compound of the formula (II) to the 1-aryl-3-alkyl-4-carboxaldehyde-5-chloropyrazol compound of the formula (IV) in one step by Vilsmeier treatment in the presence of $POCl_3$ and DMF, and
(d) in a second step, successively treating the compound of the formula (IV) with diaminomaleonitrile and then with a hypochlorite.

20. The method of claim 19, wherein step (d) is carried out in a hydroxylated aliphatic solvent medium, with, firstly, for the formation of the imine with diaminomaleonitrile, a molar concentration of substrate of between 0.15 and 0.2 M, with an acid catalyst present in proportions of between 0.02 and 0.2 molar equivalent; and then, secondly, for oxidative cyclization and formation of the imidazolyl ring, dilution to a molar concentration of substrate of between 0.01 and 0.08 M, and the use of 2 to 3 molar equivalents of sodium hypochlorite having a concentration ranging from 2 M to 5 M.

21. The method of claim 20, wherein the acid catalyst is trifluoroacetic acid.

22. The method of claim 1, wherein in the formula (I), n=0.

23. The method of claim 1, wherein one or more of the following conditions are met:

$R_1$ to $R_5$ which are identical or different, represent a group selected from the group consisting of:
- a hydrogen atom,
- a halogen atom, and
- a linear or branched, saturated or unsaturated alkyl radical $R_7$, optionally substituted with one or more halogen atoms, which are identical or different, the alkyl radical comprising 1 to 4 carbon atoms, $R_6$ represents a linear or branched, saturated or unsaturated alkyl radical comprising from 1 to 4 carbon atoms.

24. The method of claim 1, wherein one or more of the following conditions are met:

$R_1$ to $R_5$ which are identical or different, represent a group selected from the group consisting of:
- a hydrogen atom,
- a chlorine atom, and
- a linear or branched, saturated or unsaturated alkyl radical $R_7$, optionally substituted with one or more fluorine atoms, the alkyl radical comprising 1 to 4 carbon atoms, $R_6$ represents a radical selected from the group consisting of methyl, ethyl, tert-butyl and isopropyl.

25. The method of claim 1, wherein the compound of the formula (I) is selected from the group consisting of:
- 5-chloro-1-(2,6-dichloro-4-trifluoromethylphenyl)-4-(4,5-dicyano-1H-imidazol-2-yl)-3-methyl-1H-pyrazol,
- 5-chloro-1-(2,6-dichloro-4-trifluoromethylphenyl)-4-(4,5-dicyano-1H-imidazol-2-yl)-3-isopropyl-1H-pyrazol,
- 5-chloro-1-(2,6-dichloro-4-trifluoromethylphenyl)-4-(4,5-dicyano-1H-imidazol-2-yl)-3-ethyl-1H-pyrazol, and
- 5-chloro-1-(2,6-dichloro-4-trifluoromethylphenyl)-4-(4,5-dicyano-1H-imidazol-2-yl)-3-tert-butyl-1H-pyrazol.

\* \* \* \* \*